(12) United States Patent
Wigglesworth et al.

(10) Patent No.: US 9,123,899 B2
(45) Date of Patent: Sep. 1, 2015

(54) SEMICONDUCTOR COMPOUND

(75) Inventors: Anthony J. Wigglesworth, Oakville (CA); Yiliang Wu, Oakville (CA); Ping Liu, Mississauga (CA)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 400 days.

(21) Appl. No.: 13/024,425

(22) Filed: Feb. 10, 2011

(65) Prior Publication Data
US 2012/0205629 A1 Aug. 16, 2012

(51) Int. Cl.
H01L 51/00 (2006.01)
C07D 471/06 (2006.01)
H01L 51/05 (2006.01)

(52) U.S. Cl.
CPC .......... H01L 51/0072 (2013.01); C07D 471/06 (2013.01); *H01L 51/0076* (2013.01); *H01L 51/0541* (2013.01); *H01L 51/0545* (2013.01)

(58) Field of Classification Search
CPC .................................................. C07D 471/02
USPC .................................................. 546/38, 41
See application file for complete search history.

(56) References Cited

U.S. PATENT DOCUMENTS

| | | | | |
|---|---|---|---|---|
| 5,281,489 | A * | 1/1994 | Mori et al. | 428/690 |
| 5,748,271 | A * | 5/1998 | Hikmet et al. | 349/69 |
| 6,835,471 | B2 * | 12/2004 | Tsuboyama et al. | 428/690 |
| 6,858,271 | B1 * | 2/2005 | Okada et al. | 428/1.4 |
| 6,897,913 | B2 * | 5/2005 | Tsuboyama et al. | 349/61 |
| 2009/0289248 | A1 | 11/2009 | Kobayashi et al. | |
| 2010/0013381 | A1 | 1/2010 | Stoessel et al. | |

OTHER PUBLICATIONS

Kobayashi et al., "Stable peri-Xanthenoxanthene Thin-Film Transistors with Efficient Carrier Injection," Chem. Mater. 2009, 21, 552-556.

Fabbri et al, "Preparation of Enantiomerically Pure 1,1'-Binaphthalene-2,2'-diol and 1,1'Binaphthalene-2,2'-dithiol," J. Org. Chem. 1993, 58, 1748-1750.

Asari et al, "Charge-Transfer Complexes of PXX (PXX = 6, 12-Dioxaanthanthrene). The Formal Charge and Molecular Geometry," Bull. Chem. Soc. Jpn., 74, 53-58 (2001).

Haryono et al., "Synthesis of a Novel Oligo(p-phenylene) Ladder by Sulfide and Sulfonio Groups," Macromolecules 1999, 32, 3146-3149.

Sirringhaus et al., "Dibenzothienobisbenzothiophene—a novel fused-ring oligomer with high field-effect mobility," J. Mater. Chem. 1999, 9, 2095-2101.

Wu et al., U.S. Appl. No. 12/977,464, filed Dec. 23, 2010.

\* cited by examiner

*Primary Examiner* — Marie R. Yamnitzky
(74) *Attorney, Agent, or Firm* — Harness, Dickey & Pierce, P.L.C.

(57) ABSTRACT

A semiconducting tetrahydroacridinoacridine compound of Formula (I):

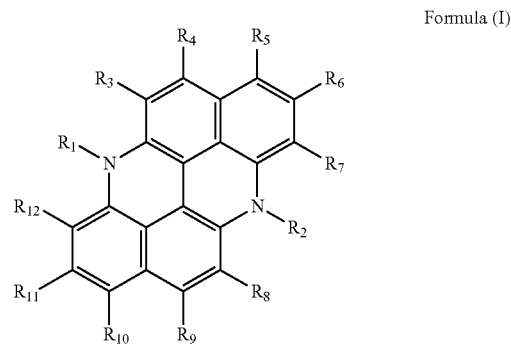

Formula (I)

wherein $R_1$ to $R_{12}$ are as described herein. The compounds are designed to ensure air stability, good solubility, and high mobility.

6 Claims, 3 Drawing Sheets
(1 of 3 Drawing Sheet(s) Filed in Color)

SEMICONDUCTOR COMPOUND

BACKGROUND

The present disclosure relates to thin-film transistors (TFTs) and/or other electronic devices comprising a semiconducting layer. The semiconducting layer is formed from a semiconductor composition as described herein. When the composition is used in the semiconducting layer of a device, high mobility and excellent stability may be achieved.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility. This poor performance may be attributable to the poor film-forming nature of small molecules.

It would be desirable to develop semiconducting compounds that exhibit high field effect mobility, air stability, and good solubility.

BRIEF DESCRIPTION

The present application discloses, in various embodiments, acridinoacridine compounds of Formula (I):

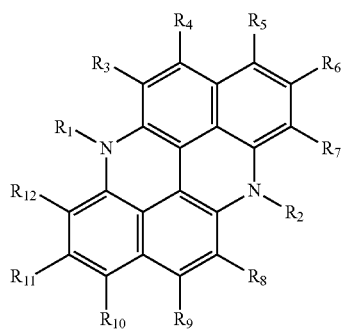

Formula (I)

wherein $R_1$ and $R_2$ are independently selected from the group consisting of hydrogen, an alkyl group, a substituted alkyl group, an aryl group, and a substituted aryl group; and wherein $R_3$ to $R_{12}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen; and wherein the semiconductor of Formula (I) is predominantly crystalline or liquid crystalline. The compounds are designed to ensure air stability, good solubility, and high mobility.

In some embodiments, $R_1$ and $R_2$ are the same and at least one of $R_3$ to $R_{12}$ is not hydrogen. $R_5$ and $R_{10}$ are usually the same. In further embodiments, $R_1$ and $R_2$ are the same and are not hydrogen. In additional embodiments, $R_1$ and $R_2$ are the same and are not hydrogen; $R_3$, $R_4$, $R_6$, $R_7$, $R_8$, $R_9$, $R_{11}$ and $R_{12}$ are hydrogen; and $R_5$ and $R_{10}$ are the same. In such embodiments, $R_5$ and $R_{10}$ sometimes are not hydrogen as well.

In some embodiments, $R_1$ and $R_2$ are independently selected from the group consisting of an alkyl group, an aryl group, and a substituted aryl group; and $R_3$ to $R_{12}$ are hydrogen.

Sometimes, $R_1$ and $R_2$ are the same, and in further embodiments may be independently alkyl or aryl.

In embodiments, $R_1$ and $R_2$ are alkyl and at least one of $R_3$ to $R_{12}$ is not hydrogen.

For field-effect transistor applications, the acridinoacridine compounds of Formula (I) are desirably crystalline, or liquid crystalline.

Also disclosed are semiconductor compositions comprising a polymer binder; and a semiconductor compound of Formula (I):

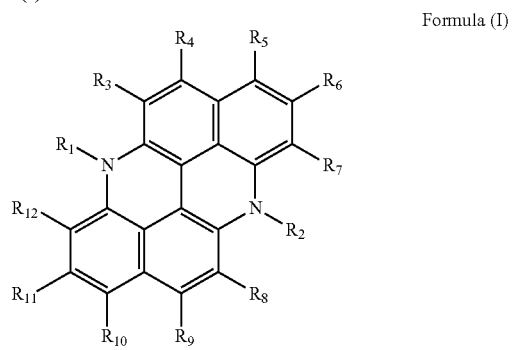

Formula (I)

wherein $R_1$ and $R_2$ are independently selected from the group consisting of a hydrogen, an alkyl group, a substituted alkyl group, an aryl group, and a substituted aryl group; and wherein $R_3$ to $R_{12}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen.

The polymer binder may be selected from the group consisting of polymethylmethacrylate, polystyrene, poly(α-methyl styrene), poly(4-methyl styrene), poly(alpha-methyl styrene-co-vinyl toluene), polystyrene-block-butadiene-block-styrene), poly(styrene-block-isopene-block-styrene), poly (vinyl toluene), poly (vinyl naphthalene), poly (vinyl pyridine), terpene resin, poly(styrene-co-2,4-dimethylstyrene), poly(chlorostyrene), poly(styrene-co-a-methyl styrene), poly (styrene-co-butadiene), polycarbazole, polytriarylamine, poly(N-vinylcarbazole), polythiophene, and a mixture thereof The polymer binder may be a styrene-based polymer. The styrene based polymer may have a weight average molecular weight of from about 40,000 to about 2,000,000.

In some embodiments, the weight ratio of the small molecule semiconductor to the polymer binder is from 5:1 to 2:3.

In some embodiments, $R_1$ and $R_2$ are not hydrogen; $R_3$, $R_4$, $R_6$, $R_7$, $R_8$, $R_9$, $R_{11}$, and $R_{12}$ are hydrogen; and $R_5$ and $R_{10}$ are the same.

Disclosed in other embodiments are electronic devices comprising a semiconducting layer, wherein the semiconducting layer comprises a small molecule semiconductor of Formula (I):

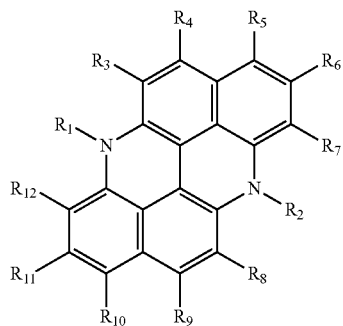

Formula (I)

wherein $R_1$ and $R_2$ are independently selected from the group consisting of hydrogen, an alkyl group, a substituted alkyl group, an aryl group and a substituted aryl group; and wherein $R_3$ to $R_{12}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen; and wherein the semiconductor of Formula (I) is predominantly crystalline or liquid crystalline.

The semiconducting layer may further comprise a polymer binder. The polymer binder may be polystyrene, poly(α-methyl styrene), poly(4-methyl styrene), poly(alpha-methyl styrene-co-vinyl toluene), polystyrene-block-butadiene-block-styrene), poly(styrene-block-isoprene-block-styrene), poly(vinyl toluene), a terpene resin, poly(styrene-co-2,4-dimethylstyrene), poly(chlorostyrene), poly(styrene-co-a-methyl styrene), poly(styrene-co-butadiene), a polycarbazole, a polytriarylamine, poly(N-vinylcarbazole), or a mixture thereof.

In some embodiments, the polymer binder is a styrene-based polymer. The styrene-based polymer may have a weight average molecular weight of from about 40,000 to about 2,000,000.

The electronic device may further comprise a dielectric layer. The dielectric layer may comprise a modified surface and the semiconducting layer may be in direct contact with the modified surface. In some embodiments, the modified surface has been modified with an organosilane.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
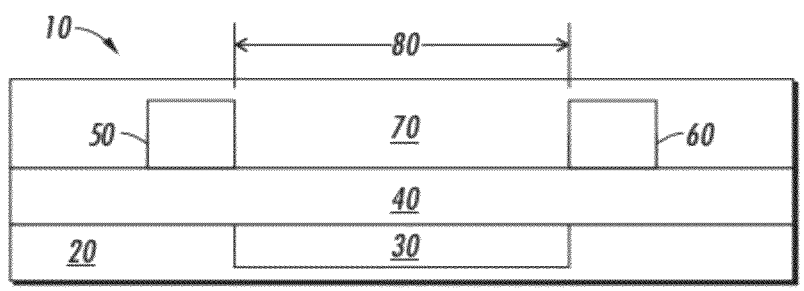
FIG. 1 is a diagram of a first embodiment of a TFT according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The term "predominantly" refers to a value of greater than 50%.

The present disclosure relates to small molecule semiconductor compounds as disclosed herein. The small molecule compounds exhibit good solubility. Compositions comprising a polymer binder and the small molecule semiconductor are also disclosed. A semiconducting layer formed from the composition is very stable in air and has high mobility. These semiconductor compositions are useful for forming layers in electronic devices, such as thin-film transistors (TFTs).

FIG. 1 illustrates a bottom-gate bottom-contact TFT configuration according to the present disclosure. The TFT 10 comprises a substrate 16 in contact with the gate electrode 18 and a gate dielectric layer 14. The gate electrode 18 is depicted here atop the substrate 16, but the gate electrode could also be located in a depression within the substrate. It is important that the gate dielectric layer 14 separates the gate electrode 18 from the source electrode 20, drain electrode 22, and the semiconducting layer 12. The semiconducting layer 12 runs over and between the source and drain electrodes 20 and 22. The semiconductor has a channel length between the source and drain electrodes 20 and 22.

Figure 2:
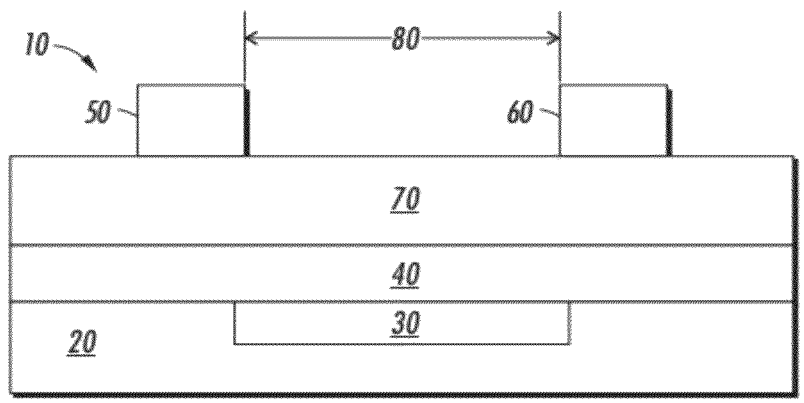
FIG. 2 is a diagram of a second embodiment of a TFT according to the present disclosure.

FIG. 2 illustrates another bottom-gate top-contact TFT configuration according to the present disclosure. The TFT 30 comprises a substrate 36 in contact with the gate electrode 38 and a gate dielectric layer 34. The semiconducting layer 32 is placed on top of the gate dielectric layer 34 and separates it from the source and drain electrodes 40 and 42.

Figure 3:
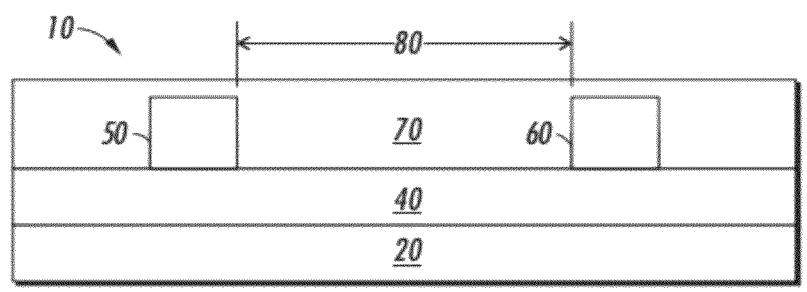
FIG. 3 is a diagram of a third embodiment of a TFT according to the present disclosure.

FIG. 3 illustrates a bottom-gate bottom-contact TFT configuration according to the present disclosure. The TFT 50 comprises a substrate 56 which also acts as the gate electrode and is in contact with a gate dielectric layer 54. The source electrode 60, drain electrode 62, and semiconducting layer 52 are located atop the gate dielectric layer 54.

Figure 4:
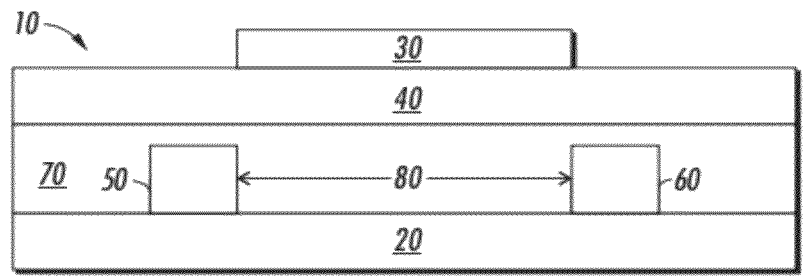
FIG. 4 is a diagram of a fourth embodiment of a TFT according to the present disclosure.

FIG. 4 illustrates a top-gate top-contact TFT configuration according to the present disclosure. The TFT 70 comprises a substrate 76 in contact with the source electrode 80, drain electrode 82, and the semiconducting layer 72. The semiconducting layer 72 runs over and between the source and drain electrodes 80 and 82. The gate dielectric layer 74 is on top of the semiconducting layer 72. The gate electrode 78 is on top of the gate dielectric layer 74 and does not contact the semiconducting layer 72.

The small molecule semiconductor has the structure of Formula (I):

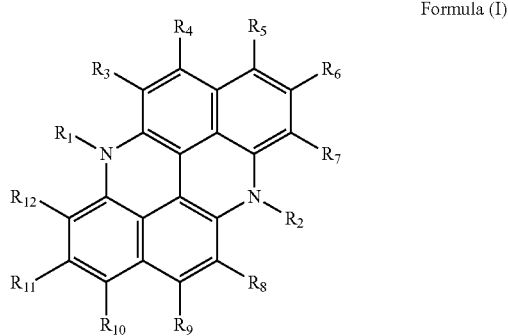

Formula (I)

wherein $R_1$ and $R_2$ are independently selected from the group consisting of hydrogen, an alkyl group, a substituted alkyl group, an aryl group, and a substituted aryl group; and wherein $R_3$ to $R_{12}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen.

Formula (I-A) shows the compound of Formula (I) with the carbons atoms numbered:

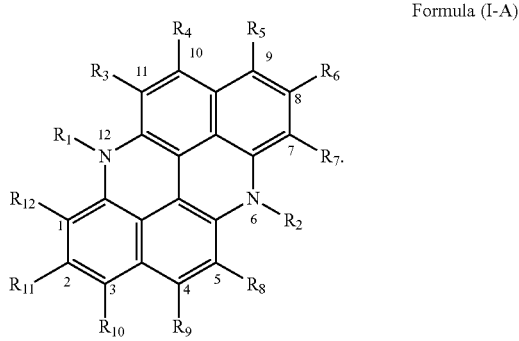

Formula (I-A)

This compound is also known as 3,6,9,12-tetrasubstituted acridinoacridine when none of $R_1$, $R_2$, $R_3$, and $R_4$ is hydrogen. The acridinoacridine core may be abbreviated herein as "AA". For example, the small molecule semiconductor of Formula (I) could be referred to as 3,6,9,12-tetrasubstituted-AA when none of $R_1$, $R_2$, $R_5$, and $R_{10}$ is hydrogen.

The term "alkyl" refers to a radical composed entirely of carbon atoms and hydrogen atoms which is fully saturated. The alkyl radical may be linear, branched, or cyclic.

The term "alkenyl" refers to an aromatic radical composed entirely of carbon atoms and hydrogen atoms which contains at least one carbon-carbon double bond that is not part of an aryl or heteroaryl structure. The alkenyl radical may be linear, branched, or cyclic.

The term "ethynyl" refers to a radical having the formula —C≡CH.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to a cyclic radical composed of carbon atoms, hydrogen atoms, and a heteroatom within a ring of the radical, the cyclic radical being aromatic. The heteroatom may be nitrogen, sulfur, or oxygen. Exemplary heteroaryl groups include thienyl (an aromatic radical of the formula —$C_4H_3S$ formed by removing a hydrogen atom from thiophene), pyridinyl, and quinolinyl. When heteroaryl is described in connection with a numerical range of carbon atoms, it should not be construed as including substituted heteroaromatic radicals.

The term "alkoxy" refers to an alkyl radical which is attached to an oxygen atom, i.e. —O—$C_nH_{2n+1}$.

The term "alkylthio" refers to an alkyl radical which is attached to a sulfur atom, i.e. —S—$C_nH_{2n+1}$.

The term "trialkylsilyl" refers to a radical composed of a tetravalent silicon atom having three alkyl radicals attached to the silicon atom, i.e. —$Si(R)_3$. The three alkyl radicals may be the same or different. The three alkyl radicals may be substituted.

The term "fluorohydrocarbon" refers to a radical composed entirely of fluorine, hydrogen, and carbon atoms. At least one fluorine atom must be present. The radical can be linear or branched, and is usually saturated.

The term "substituted" refers to at least one hydrogen atom on the named radical being substituted with another functional group, such as halogen, —CN, —$NO_2$, —COOH, and —$SO_3H$. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an alkyl, alkenyl, or ethynyl group may also be substituted with an aryl or heteroaryl group. An exemplary substituted alkenyl group is phenylethenyl (—CH=CH—$C_6H_5$). An exemplary substituted ethynyl group is phenylethynyl (—C≡C—$C_6H_5$). An aryl or heteroaryl group may also be substituted with alkyl or alkoxy. Exemplary substituted aryl groups include methylphenyl and methoxyphenyl. Exemplary substituted heteroaryl groups include 3-methylthienyl.

Generally, the alkyl and alkoxy groups each independently contain from 1 to 30 carbon atoms. Similarly, the aryl group may contain from 6 to 30 carbon atoms. Heteroaryl groups may contain from 5 to 25 carbon atoms.

As noted above, $R_1$-$R_{12}$ may be the same or different. In some embodiments, $R_1$ and $R_2$ are the same, or $R_5$ and $R_{10}$ are the same. In particular embodiments, $R_1$ and $R_2$ may be the same or different alkyl. In more specific embodiments, $R_1$ and $R_2$ are the same $C_4$-$C_{16}$ alkyl, particular $C_6$ alkyl, i.e. hexyl. In embodiments, $R_5$ and $R_{10}$ may be the same or different aryl. In more specific embodiments, $R_5$ and $R_{10}$ are both phenyl.

The compound of Formula (I) is preferably predominantly crystalline or liquid crystalline. The compound or semiconducting layers formed from the compound may exhibit a crystallinity greater than about 50%. In embodiments, the compound or semiconducting layer may have a crystallinity of greater than about 80%, or greater than about 90%. The crystallinity of the semiconductor layer can be determined using any suitable method, for example an X-ray diffraction method.

The term liquid crystalline refers to compounds which have at least two melting points. The phase transition temperatures can be determined using any suitable method, for example by a differential scanning calorimetry method. In contrast, crystalline compounds have only one melting point.

In embodiments, the small molecule semiconductor has a band gap of from about 1.8 to about 3.2 eV. This band gap typically means that the small molecule semiconductor has better stability in air, when compared to a pentacene-based semiconductor. The small molecule semiconductor has a crystalline, or liquid crystalline structure.

Methods of producing the small molecule semiconductor of Formula (I) generally begin with the synthesis of the acridinoacridine (AA) compound. It is believed that hydrogen atoms at the 3-, 6-, 9- and/or 12-positions of the AA compound can then be replaced with the desired substituents. The AA compound is shown below with the substituent positions numbered:

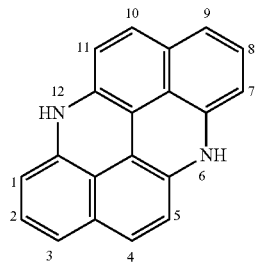

The AA core may be formed from the three step scheme illustrated below. In the first step, N-(7-hydroxynaphthalen-1-yl)acetamide 1 is dimerized to produce a binaphthol derivative 2.

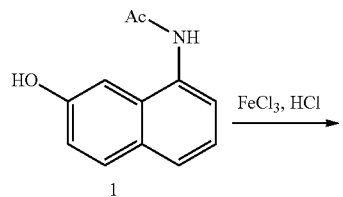

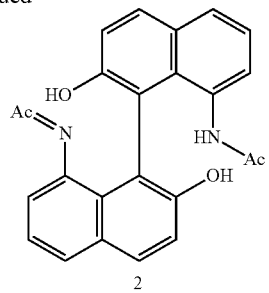

Next, the binaphthol derivative 2 undergoes deprotection at acidic conditions to replace the acetyl groups with hydrogen atoms and produce compound 3.

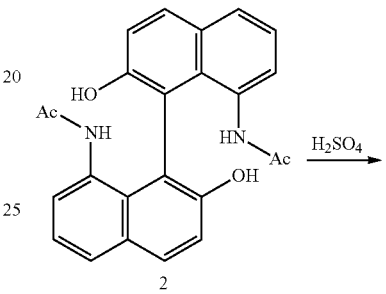

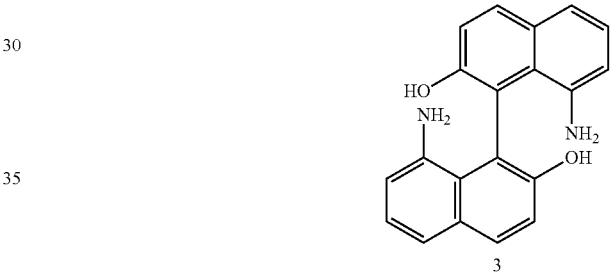

Compound 3 then undergoes Cu(II) mediated double cyclization to produce the AA core.

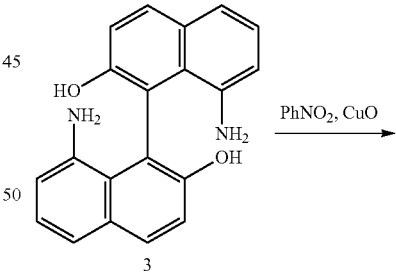

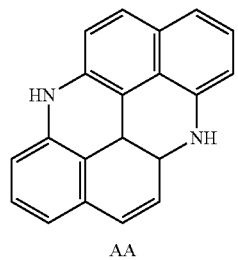

It is believed that the AA core compound can be functionalized, i.e. substituted, at the 3-, 6-, 9-, and/or 12-positions by a variety of methods. One such method is disclosed below.

The AA core compound is first N-alkylated with hexylbromide to yield a soluble dihexyl derivative 4.

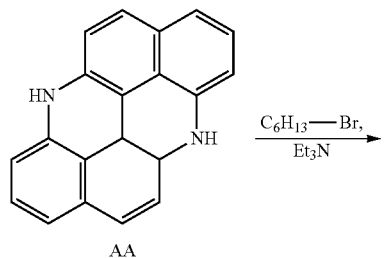

The soluble dihexyl derivative 4 is brominated with diatomic bromine and/or N-bromosuccinimide to form compound 5.

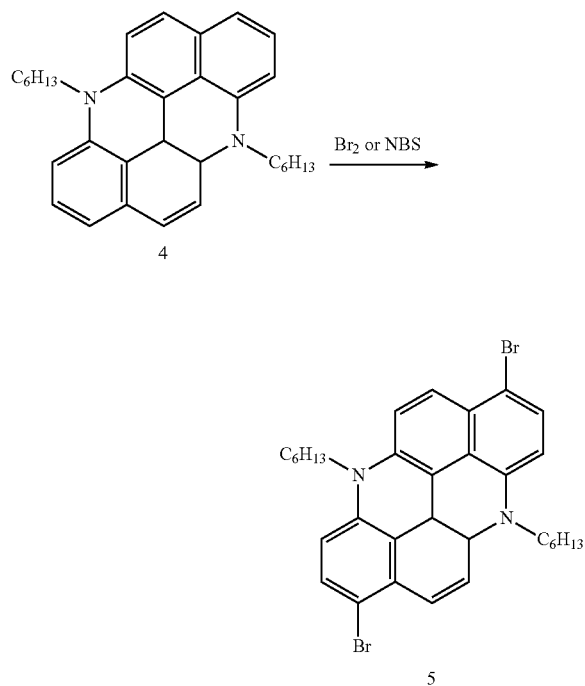

Compound 5 undergoes Suzuki-Miyaura cross-coupling with arylboronic acids to produce tetrasubstituted derivative 6.

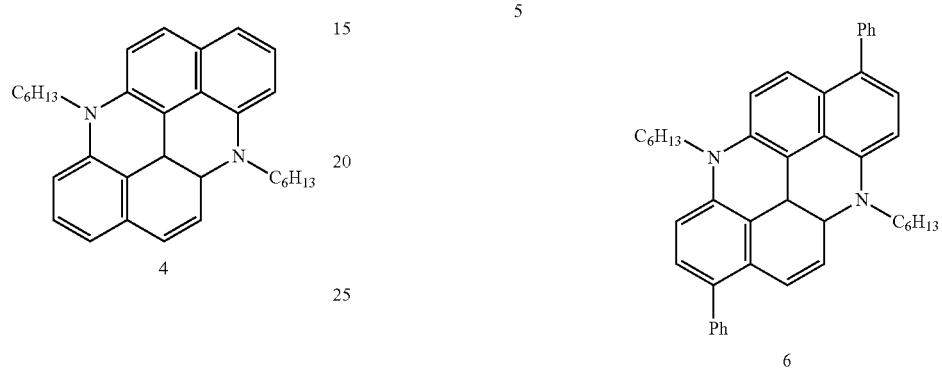

While the exemplary small molecule semiconductor is tetrasubstituted, monosubstituted, disubstituted, trisubstituted, pentasubstituted, and hexasubstituted compounds can also be produced via similar reactions.

Figure 5:
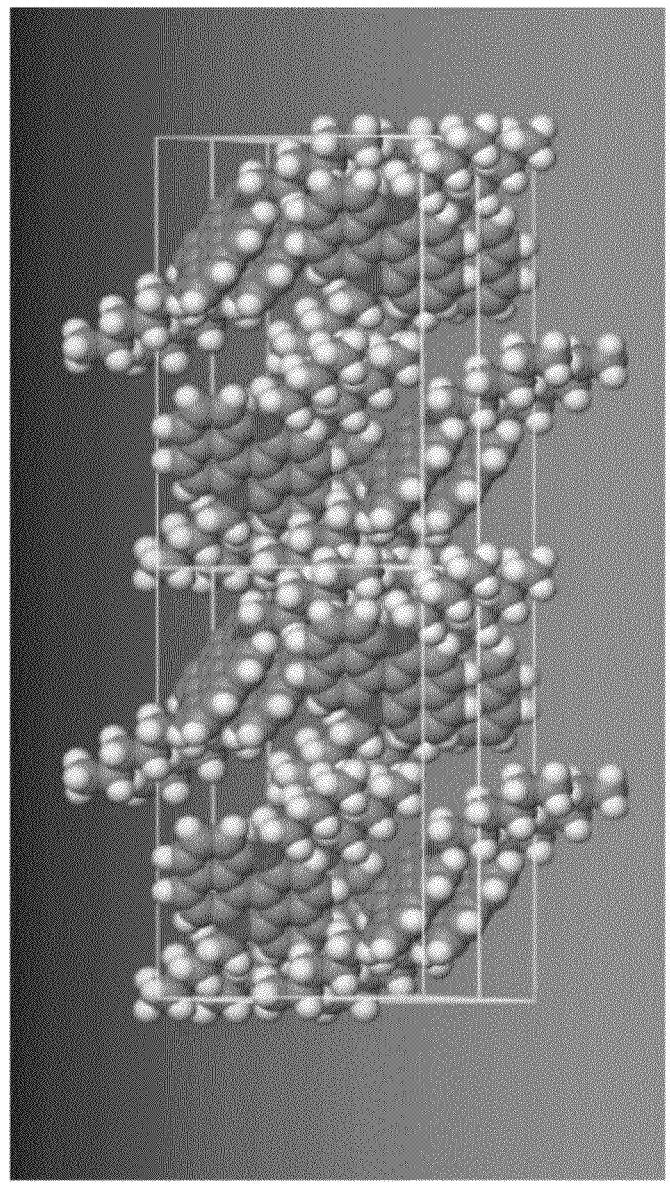
FIG. 5 shows a color model of the equilibrium geometry and crystal structure of 6,12-dihexyl-acridinoacridine.

FIG. 5 illustrates a color molecular model of 6,12-dihexyl AA, i.e. a compound of Formula (I) wherein $R_1$ and $R_3$ are hexyl. The model shows the equilibrium geometry and crystal structure of the compound. The model formed in Materials Studio 5.0 using the DMol3 package and the crystal structure prediction was performed using the Polymorph module. Without being bound by theory, it is believed that the nitrogen heteroatoms aid stability, the extended heteroacene core enhances orbital overlap, and the substitutions at the 6- and 12-positions aid solubility and enhance solid-state packing. The compounds are designed to ensure air stability, good solubility, and high mobility. Electronic devices including a semiconducting layer comprising the compounds may be produced at a low cost under ambient conditions.

The small molecule semiconductor by itself may have poor film-forming properties. Thus, a semiconductor composition may be formed that comprises the small molecule semiconductor of Formula (I) and a polymer binder. This allows a uniform film to be achieved, significantly improving device performance. The polymer binder can be considered as forming a matrix within which the small molecule semiconductor is dispersed.

Any suitable polymer can be used as the polymer binder for the semiconductor composition. In some embodiments, the polymer is an amorphous polymer. The amorphous polymer may have a glass transition temperature less than the melting point temperature of the small molecule semiconductor. In embodiments, the polymer has a dielectric constant less than 4.5, preferably less than 3.5, including less than 3.0, as measured at 60 Hz at room temperature.

In embodiments, the polymer is selected from polymers containing only C, H, F, Cl, and/or N atoms. In some embodiments, the polymer is a low polarity polymer such as a hydrocarbon polymer or a fluorocarbon polymer without any polar groups. For example, polystyrene is an amorphous polymer and has a dielectric constant of about 2.6. A list of other low polarity polymers includes, but is not limited to, the following: fluoropolyarylether, poly (p-xylylene), poly(vinyl toluene), poly (α-methyl styrene), poly(vinylnaphthalene), polyethylene, polypropylene, polyisoprene, poly(tetrafluoroethylene), poly(chlorotrifluoroethylene), poly(2-methyl-1,3-butadiene), poly (cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane)bis-(4-phenyl)carbonate], poly(α-α-α'-α' tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-α-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isoprene-block-styrene), terpene resin, poly(N-vinylcarbazole), polycarbazole, polytriarylamine, and the like.

In some embodiments, the polymer binder is selected from polymethylmethacrylate, polystyrene, poly(α-methyl styrene), poly(4-methyl styrene), poly(α-methyl styrene-co-vinyl toluene), poly(styrene-block-butadiene-block-styrene), poly(styrene-block-isopene-block-styrene), poly (vinyl toluene), poly (vinyl naphthalene), poly (vinyl pyridine), a terpene resin, poly(styrene-co-2,4-dimethylstyrene), poly(chlorostyrene), poly(styrene-co-α-methyl styrene), poly(styrene-co-butadiene), polycarbazole, a polytriarylamine, poly(N-vinylcarbazole), a polythiophene, and a mixture thereof.

In some embodiments, the polymer binder is a styrene-based polymer. Styrene-based polymers contain a repeating unit derived from a styrene monomer of Formula (II):

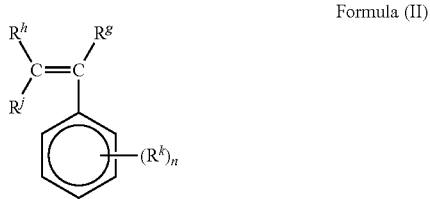

Formula (II)

wherein $R^g$, $R^h$, $R^j$, and $R^k$ are independently hydrogen, halogen, and $C_1$-$C_{20}$ alkyl; and n is an integer from 0 to 5. The styrene monomer can be styrene ($R^g$, $R^h$, and $R^j$ are all hydrogen, n=0), alpha-methyl styrene ($R^g$ is methyl, $R^h$ and $R^j$ are hydrogen, n=0), or 4-methyl styrene ($R^g$, $R^h$, and $R^j$ are all hydrogen, n=1, $R^k$ is methyl in the 4-position).

The styrene-based polymer may have a weight average molecular weight of from about 40,000 to about 2,000,000.

The weight ratio of the small molecule semiconductor to the polymer binder may be from 5:1 to 2:3.

The semiconductor composition may further comprise a solvent in which the small molecule semiconductor and the polymer binder are soluble. Exemplary solvents used in the solution may include chlorinated solvents such as chlorobenzene, chlorotoluene, dichlorobenzene, dichloroethane, and the like; alcohols and diols such as propanol, butanol, hexanol, hexanediol, etc.; hydrocarbons or aromatic hydrocarbons such as hexane, heptane, toluene, xylene, ethyl benzene, etc.; ketones such as acetone, methyl ethyl ketone, etc.; acetates, such as ethyl acetate; pyridine, tetrahydrofuran, and the like.

In embodiments, the semiconductor composition comprising the small molecule semiconductor and the polymer binder may have a viscosity of from about 1.5 centipoise (cps) to about 100 cps, including from about 2 to about 20 cps.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

The performance of a TFT can be measured by mobility. The mobility is measured in units of $cm^2$/V·sec; higher mobility is desired. The resulting TFT using the semiconductor composition of the present disclosure may have a field effect mobility of at least about 0.01 $cm^2$/V·sec. The TFT of the present disclosure may have a current on/off ratio of at least about $10^3$.

A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. Exemplary surface modifiers include organosilanes such as hexamethyldisilazane (HMDS), octyltrichlorosilane (OTS-8), octadecyltrichlorosilane (ODTS-18), and phenyltrichlorosilane (PTS). The semiconducting layer can be directly contacted with this modified dielectric layer surface. The contact may be complete or partial. This surface modification can also be considered as forming an interfacial layer between the dielectric layer and the semiconducting layer.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconducting layer are on the substrate, even though one layer is closer to the substrate than the other layer. The resulting TFT has good mobility and good current on/off ratio.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. An electronic device comprising:
a dielectric layer; and
a semiconducting layer in direct contact with a surface of the dielectric layer, wherein the semiconducting layer includes a polymer binder and molecules of a semiconductor compound of Formula (I):

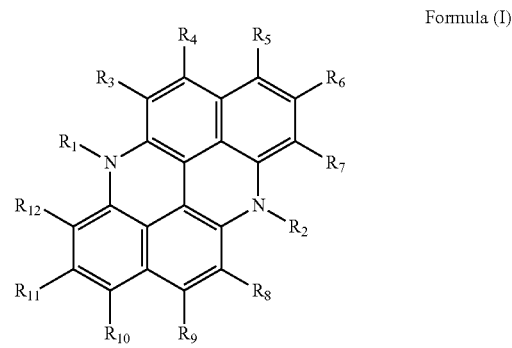

Formula (I)

wherein $R_1$ and $R_2$ are independently selected from the group consisting of hydrogen, an alkyl group, a substituted alkyl group, an aryl group, and a substituted aryl group;

wherein $R_3$ to $R_{12}$ are independently selected from the group consisting of hydrogen, an alkyl group, a substituted alkyl group, an alkoxy group, an alkylthio group, an alkenyl group, a substituted alkenyl group, an ethynyl group, a substituted ethynyl group, an aryl group, a substituted aryl group, a heteroaryl group, a substituted heteroaryl group, a trialkylsilyl group, a fluorohydrocarbon group, a cyano group, and a halogen; and wherein the molecules of the semiconductor compound of Formula (I) are predominantly crystalline or liquid crystalline in the semiconducting layer.

2. The electronic device of claim 1, wherein $R_1$ and $R_2$ are the same and are not hydrogen.

3. The electronic device of claim 2, wherein $R_3$, $R_4$, $R_6$, $R_7$, $R_8$, $R_9$, $R_{11}$ and $R_{12}$ are hydrogen; and wherein $R_5$ and $R_{10}$ are the same.

4. The electronic device of claim 1, wherein $R_1$ and $R_2$ are independently selected from the group consisting of an alkyl group, a substituted alkyl group, an aryl group, and a substituted aryl group; and wherein $R_3$ to $R_{12}$ are hydrogen.

5. The electronic device of claim 1, wherein the polymer binder is polystyrene, poly($\alpha$-methyl styrene), poly(4-methyl styrene), poly($\alpha$-methyl styrene-co-vinyl toluene), poly(styrene-block-butadiene-block-styrene), poly(styrene-block-isoprene-block-styrene), poly (vinyl toluene), a terpene resin, poly(styrene-co-2,4-dimethylstyrene), poly(chlorostyrene), poly(styrene-co-$\alpha$-methyl styrene), poly(styrene-co-butadiene), a polycarbazole, a polytriarylamine, a poly(N-vinylcarbazole), or a mixture thereof.

6. The electronic device of claim 1, wherein the surface of the dielectric layer is modified by an organosilane.

* * * * *